(12) United States Patent
Euler

(10) Patent No.: US 10,371,688 B2
(45) Date of Patent: Aug. 6, 2019

(54) SENSING SYSTEM BASED ON A FLUOROPHORE ARRAY

(71) Applicant: Rhode Island Board of Education, State of Rhode Island and Providence Plantations, Providence, RI (US)

(72) Inventor: William B. Euler, Narragansett, RI (US)

( * ) Notice: Subject to any disclaimer, the term of this patent is extended or adjusted under 35 U.S.C. 154(b) by 28 days.

(21) Appl. No.: 15/430,320

(22) Filed: Feb. 10, 2017

(65) Prior Publication Data

US 2017/0227515 A1 Aug. 10, 2017

Related U.S. Application Data

(60) Provisional application No. 62/293,696, filed on Feb. 10, 2016.

(51) Int. Cl.
*G01N 33/22* (2006.01)
*G01N 33/00* (2006.01)
*G01N 21/64* (2006.01)

(52) U.S. Cl.
CPC ......... *G01N 33/227* (2013.01); *G01N 21/643* (2013.01); *G01N 33/0057* (2013.01); *G01N 2021/6432* (2013.01)

(58) Field of Classification Search
CPC ...... G01N 33/227; G01N 33/22; G01N 33/00; G01N 33/0057; G01N 33/0027; G01N 33/0009; G01N 33/0004; G01N 21/643; G01N 21/6428; G01N 21/64; G01N 21/63; G01N 21/62

USPC ...... 422/50, 400, 401, 402, 83, 88; 436/110, 436/106

See application file for complete search history.

(56) References Cited

U.S. PATENT DOCUMENTS

2005/0101026 A1 5/2005 Sailor et al.
2009/0246881 A1 10/2009 Toal et al.
2010/0245081 A1 9/2010 Arcaini et al.
(Continued)

OTHER PUBLICATIONS

Matoian, Meredith A., Developing a Method for Enhanced Explosive Detection by Surface Enhanced Raman Scattering (SERS) and Metal Enhanced Fluorescence (MEF), (2013). Open Access Master's Theses. Paper 4. (Year: 2013).*
(Continued)

*Primary Examiner* — Christine T Mui
(74) *Attorney, Agent, or Firm* — Milstein Zhang & Wu LLC; Duan Wu, Esq.

(57) ABSTRACT

A sensing system for explosives is provided. The sensor is based on a layered structure of approximately a monolayer of a fluorophore deposited onto a few nm of a transparent polymer, supported by a substrate. The fluorophores can be xanthene laser dyes, which have high quantum yields, and the polymers can be commodity materials polymethylmethacrylate and polyvinylidene difluoride. The different fluorophore/polymer combinations give different emission responses to analytes, including both signal quenching and enhancement. The pattern of responses can be used to identify the analyte. The common explosives TNT, PETN, RDX, HMX, and TATP as gas phase species can all be uniquely identified at room temperature using only the natural vapor pressure of the explosive to deliver sample to the sensor.

24 Claims, 8 Drawing Sheets

(56) References Cited

U.S. PATENT DOCUMENTS

2012/0304729 A1    12/2012   O'Dell et al.
2015/0147818 A1     5/2015   Kim et al.

OTHER PUBLICATIONS

Latendresse, Christopher A., "Chemical Reactions of Explosive Molecules for Detection Applications" (2013). Open Access Dissertations. Paper 60. (Year: 2013).*

Latendresse, Christopher A. et al, A fluorometric sensing array for the detection of military explosives and IED materials†, Anal. Methods, 2013, 5, 5457-5463. (Year: 2013).*

K. Aslan et al. "Metal-enhanced fluorescence: an emerging tool in biotechnology" Current Opinion in biotechnology 2005, 16:55-62.

M. Matoian et al. "Light Trapping to Amplify Metal Enhanced Fluorescence with Application for Sensing TNT" J Fluoresc 2013, 23:877-880.

S. Yang et al., "Fluorescence Modulation by Absorbent on Solid Surface: An Improved Approach for Designing Fluorescent Sensor" Anal. Chem., 2014, 86:7931-7938.

X. Sun et al., "Florescence based explosive detection: from mechanisms to sensory materials" Chem. Soc Rev., 2015 44:8019-8061.

C. Latendresse et al. "A fluorometric sensing array for the detection of military explosives and IED materials" Anal Methods, 2013, 5:5457-5463.

* cited by examiner

| Polymer | Refractive Index |
|---|---|
| Poly(methacrylic acid), sodium salt | 1.4010 |
| Poly(dimethyl siloxane) | 1.4035 |
| Poly(trifluoroethyl acrylate) | 1.4070 |
| Poly(2-(1,1,2,2-tetrafluoroethoxy)ethyl acrylate | 1.4120 |
| Poly(trifluoroisopropyl methacrylate) | 1.4177 |
| Poly(2,2,2-trifluoro-1-methylethyl methacrylate) | 1.4185 |
| Poly(2-trifluoroethoxyethyl acrylate) | 1.4190 |
| Poly(vinylidene fluoride) | 1.4200 |
| Poly(trifluoroethyl methacrylate) | 1.4370 |
| Poly(methyl octadecyl siloxane) | 1.4430 |
| Poly(methyl hexyl siloxane) | 1.4430 |
| Poly(methyl octyl siloxane) | 1.4450 |
| Poly(isobutyl methacrylate) | 1.4470 |
| Poly(vinyl isobutyl ether) | 1.4507 |
| Poly(methyl hexadecyl siloxane) | 1.4510 |
| Poly(ethylene oxide) | 1.4539 |
| Poly(vinyl ethyl ether) | 1.4540 |
| Poly(methyl tetradecyl siloxane) | 1.4550 |
| Poly(ethylene glycol mono-methyl ether) | 1.4555 |
| Poly(vinyl n-butyl ether) | 1.4563 |
| Poly(propylene oxide) | 1.4570 |
| Poly(3-butoxypropylene oxide) | 1.4580 |
| Poly(3-hexoxypropylene oxide) | 1.4590 |
| Poly(ethylene glycol) | 1.4590 |
| Poly(vinyl n-pentyl ether) | 1.4590 |
| Poly(vinyl n-hexyl ether) | 1.4591 |
| Poly(4-fluoro-2-trifluoromethylstyrene) | 1.4600 |
| Poly(vinyl octyl ether) | 1.4613 |
| Poly(vinyl n-octyl acrylate) | 1.4613 |
| Poly(vinyl 2-ethylhexyl ether) | 1.4626 |
| Poly(vinyl n-decyl ether) | 1.4628 |
| Poly(2-methoxyethyl acrylate) | 1.4630 |
| Poly(acryloxypropyl methyl siloxane) | 1.4630 |
| Poly(4-methyl-1-pentene) | 1.4630 |
| Poly(3-methoxypropylene oxide) | 1.4630 |
| Poly(t-butyl methacrylate) | 1.4638 |
| Poly(vinyl n-dodecyl ether) | 1.4640 |
| Poly(3-ethoxypropyl acrylate) | 1.4650 |
| Poly(vinyl propionate) | 1.4664 |
| Poly(vinyl acetate) | 1.4665 |
| Poly(vinyl propionate) | 1.4665 |
| Poly(vinyl methyl ether) | 1.4670 |
| Poly(ethyl acrylate) | 1.4685 |
| Poly(vinyl methyl ether) (isotactic) | 1.4700 |
| Poly(3-methoxypropyl acrylate) | 1.4710 |
| Poly(1-octadecene) | 1.4710 |
| Poly(2-ethoxyethyl acrylate) | 1.4710 |
| Poly(isopropyl acrylate) | 1.4728 |
| Poly(1-decene) | 1.4730 |
| Poly(propylene) (atactic) | 1.4735 |
| Poly(lauryl methacrylate) | 1.4740 |
| Poly(vinyl sec-butyl ether) (isotactic) | 1.4740 |
| Poly(n-butyl acrylate) | 1.4740 |
| Poly(dodecyl methacrylate) | 1.4740 |
| Poly(ethylene succinate) | 1.4744 |
| Poly(tetradecyl methacrylate) | 1.4746 |
| Poly(hexadecyl methacrylate) | 1.4750 |
| Cellulose acetate butyrate | 1.4750 |
| Cellulose acetate | 1.4750 |
| Poly(vinyl formate) | 1.4757 |
| Ethylene/vinyl acetate copolymer-40% vinyl acetate | 1.4760 |
| Poly(2-fluoroethyl methacrylate) | 1.4768 |
| Poly(octyl methyl silane) | 1.4780 |
| Ethyl cellulose | 1.4790 |
| Poly(methyl acrylate) | 1.4793 |
| Poly(dicyanopropyl siloxane) | 1.4800 |
| Poly(oxymethylene) | 1.4800 |
| Poly(sec-butyl methacrylate) | 1.4800 |
| Poly(dimethylsiloxane-co-alpha-methyl styrene) | 1.4800 |
| Poly(n-hexyl methacrylate) | 1.4813 |
| Ethylene/vinyl acetate copolymer-33% vinyl acetate | 1.4820 |
| Poly(n-butyl methacrylate) | 1.4830 |
| Poly(ethylidene dimethacrylate) | 1.4831 |
| Poly(2-ethoxyethyl methacrylate) | 1.4833 |
| Poly(n-propyl methacrylate) | 1.4840 |
| Poly(ethylene maleate) | 1.4840 |
| Ethylene/vinyl acetate copolymer-28% vinyl acetate | 1.4845 |
| Poly(ethyl methacrylate) | 1.4850 |
| Poly(vinyl butyral) | 1.4850 |
| Poly(vinyl butyral)-11% hydroxyl | 1.4850 |
| Poly(3,3,5-trimethylcyclohexyl methacrylate) | 1.4850 |
| Poly(2-nitro-2-methylpropyl methacrylate) | 1.4868 |
| Poly(dimethylsiloxane-co-diphenylsiloxane) | 1.4880 |
| Poly(1,1-diethylpropyl methacrylate) | 1.4889 |
| Poly(triethylcarbinyl methacrylate) | 1.4889 |
| Poly(methyl methacrylate) | 1.4893 |
| Poly(2-decyl-1,4-butadiene) | 1.4899 |
| Polypropylene, isotactic | 1.4900 |
| Poly(vinyl butyral)-19% hydroxyl | 1.4900 |
| Poly(mercaptopropyl methyl siloxane) | 1.4900 |
| Poly(ethyl glycolate methacrylate) | 1.4903 |
| Poly(3-methylcyclohexyl methacrylate) | 1.4947 |
| Poly(cyclohexyl alpha-ethoxyacrylate) | 1.4969 |
| Methyl cellulose | 1.4970 |
| Poly(4-methylcyclohexyl methacrylate) | 1.4975 |
| Poly(decamethylene glycol dimethacrylate) | 1.4990 |
| Poly(vinyl alcohol) | 1.5000 |
| Poly(vinyl formal) | 1.5000 |
| Poly(2-bromo-4-trifluoromethyl styrene) | 1.5000 |
| Poly(1,2-butadiene) | 1.5000 |
| Poly(sec-butyl alpha-chloroacrylate) | 1.5000 |
| Poly(2-heptyl-1,4-butadiene) | 1.5000 |
| Poly(vinyl methyl ketone) | 1.5000 |

FIG. 3

SENSING SYSTEM BASED ON A FLUOROPHORE ARRAY

CROSS-REFERENCE TO RELATED APPLICATIONS

This application claims priority to and the benefit of co-pending U.S. provisional patent application Ser. No. 62/293,696, filed on Feb. 10, 2016, which application is incorporated herein by reference in its entirety.

STATEMENT REGARDING FEDERALLY SPONSORED RESEARCH OR DEVELOPMENT

The invention described herein was made with government support under grant nos. 2008-ST-061-ED0002 and 2013-ST-061-ED0001, awarded by U.S. Department of Homeland Security. The government has certain rights in the invention.

BACKGROUND OF THE INVENTION

Major efforts have been undertaken in the world to develop, certify and deploy explosive detection systems. In recent years, at least 2000 to 3000 explosive incidents warranting investigation have occurred within the United States and a comparable number in other countries. As the spread of terrorism rose to an alarming proportion across the globe, the need for sensitive yet reliable detection of concealed explosives has also increased exponentially.

Further, the analysis of explosives is of great importance in a variety of fields. For example, in forensic science, identification of these explosives and their degradation products can be used to identify persons in recent contact with an explosive device. In environmental protection, knowledge of explosives present in undetonated landmines can be critical in protecting the surrounding soil and groundwater as explosives can leach into and persist in the environs and pose a threat to the living inhabitants. In industrial quality control, manufacturers of explosive materials must assure consumers that their products are safe, effective and free from contamination by monitoring the composition throughout the manufacturing process.

Explosive sensors have been developed based on a number of detection technologies, such as colorimetry, fluorescence, mass spectrometry, electro-chemical methods, and Surface Enhanced Raman Scattering (SERS), and so on. However, detection of trace quantities of explosives in the gas phase has remained a significant challenge to analytical chemistry. The low vapor pressure of most explosives, in the parts per billion (ppb) to parts per trillion (ppt) ranges at room temperature, pushes the limits for most methods including modern fluorescent techniques. See S. Yang, et al., *Anal. Chem.*, 2014, 86, 7931-7938.

In earlier work, Applicant reported that xanthene dyes interact with a variety of explosives and related materials in dimethyl formamide (DMF) solution and these can be detected by changes in emission. See, C. A. Latendresse, et al., *Anal. Methods*, 2013, 5, 5457-5463. Xanthenes are readily available and inexpensive laser dyes with high quantum yields. While most of the analytes tested in our earlier work showed quenching of the fluorophore, a few of the molecules showed enhancement of the fluorescent signal, which was surprising. Except for trinitrotoluene (TNT) and trinitrobenzene (TNB), the fluorescent signal changes were modest, typically 10% or less. TNT and TNB showed large signal changes because they reacted with the DMF solvent to form highly colored products, which absorbed the emitted light.

Still, there remained a need for a more sensitive yet reliable sensor for detecting explosive-related analytes. Further, the challenge of detecting multiple analytes in their respective gas phase using strong fluorophore-based signals remained unmet.

SUMMARY OF THE INVENTION

To meet the above challenge and need, the present invention, based on a sensor array, provides means to detect a variety of explosive analytes and related materials such as impurities often found in explosives. The resulting sensing system uses a three-layer structure with a support or substrate at the bottom, a transparent layer in the middle, and on the top discreet pixels or cells each containing at least one fluorophore, e.g., a monolayer of a fluorophore. The intermediate transparent layer, in a preferred embodiment, is made of polymer and is less than about 1000 nm in thickness. As each pixel constitutes a sensor in the system, an embodiment of the sensing system, using multiple sensors, can simultaneously detect, in the presence of the same analyte in its gas phase and at room temperature, optical responses from multiple combinations where the fluorophore, the thickness of the polymeric layer, and the makeup of the polymer layer can vary. Consequently, the detected optical responses are compared to a signature pattern or profile of each target chemical, e.g., that of an explosive, for determining whether the analyte is one of the target chemicals.

Accordingly, in one aspect, the invention relates to a method for detecting an explosive or related material, preferably in its gas phase and at room temperature, using a sensing system with an array of fluorophore-based sensors containing the above-described structure for amplifying an optical response from the fluorophore in each sensor, wherein different fluorophore/polymer combinations are selected so that the optical responses from the sensors will be altered and result in both signal quenching and emission enhancement in the presence of a target explosive or related material, preferably, by more than about 5% in both cases. In a feature, the optical responses from the sensors also include a negligible or no response that is less than 5% change in emission intensity. The detection method also includes steps of exposing the sensing system to an analyte-containing sample, detecting altered optical responses from each sensor, comparing detected optical responses to a pattern known to come from a target explosive or related material; and determining they are similar enough to identify the analyte as the target explosive or related material.

In a further aspect, the invention relates to a method for detecting an explosive or related material, preferably in its gas phase and at room temperature, using a sensing system with an array of fluorophore-based sensors containing the above-described structure, wherein at least one fluorophore/polymer combination is selected such that the presence of a target explosive or related material alters an optical response that otherwise is expected from the sensor by at least about 5%, preferably at least about 10%, and further preferably at least about 20%, either in the form of signal quenching or emission enhancement.

In yet another aspect, the invention relates to a method for detecting an explosive or related material, preferably in its gas phase and at room temperature, using a sensing system with an array of fluorophore-based sensors containing the above-described structure, wherein at least two sensors in the array are selected to have respective intermediate layers that differ in thickness, thereby generating a detectable difference in their respective optical responses in the presence of the same explosive or related material. The detectable difference is, in an embodiment, the difference between at least two measurable responses selected from signal quenching, negligible change and emission enhancement. In one feature, the two intermediate layers that differ in thickness are of the same material, e.g., the same polymer.

In one embodiment, the invention provides a sensing system for detecting a chemical compound, the system comprising an array of sensors each supported on a substrate, each sensor comprising a top layer comprising a fluorophore and an intermediate layer in between the top layer and the substrate for amplifying an optical response from the fluorophore, wherein the intermediate layer is less than 1000 nm thick and has a refractive index less than that of the fluorophore, and at least two sensors in the array have respective intermediate layers that differ in thickness. The intermediate layer is preferably transparent and consists essentially of one or more polymers. In an embodiment, the two intermediate layers that differ in thickness are of the same material.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 3 lists some examples of polymers useful as the intermediate layer in an embodiment of the invention.

DETAILED DESCRIPTION OF THE INVENTION

Figure 2:
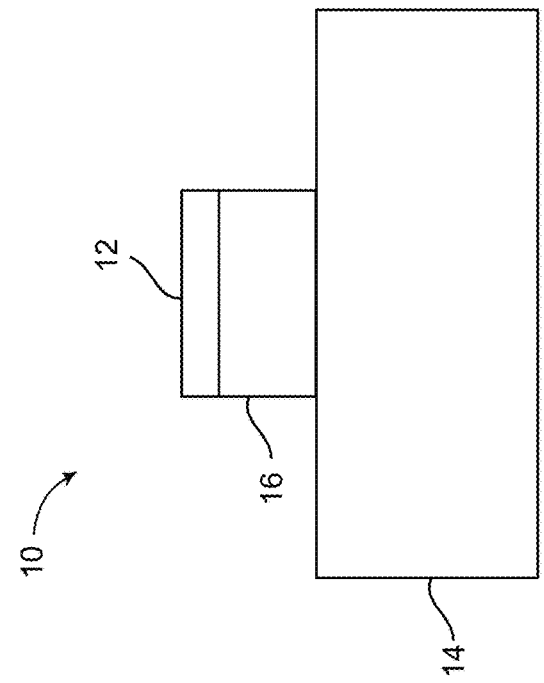
FIG. 2 illustrates a cross-sectional or cutaway view of the embodiment of FIG. 1 along the line 2-2.

As used in the specification and claims, the singular form "a", "an", or "the" includes plural references unless the context clearly dictates otherwise. For example, the term "a cell" includes a plurality of cells including mixtures thereof.

As used herein, "quantum yield" is defined as the ratio of the number of photons emitted to the number of photons absorbed by a fluorophore. The maximum fluorescence quantum yield is 1.0 or 100%. Compounds with quantum yields of 0.10 are still considered quite fluorescent. As used herein, "high quantum yield" refers to a value no less than 0.20, preferably no less than 0.50, and more preferably no less than 0.80, or even 0.90.

As used herein, "explosive chemical", "explosive analyte", "explosive material" and "explosive" refer to nitrogen-containing or other compounds that can be used to make an explosive device, including but are not limited to nitroaromatics, nitroamines, organic nitramides, and organic nitrates. "[Explosive] related material" refers to precursors, derivatives of the explosive, explosion products, or impurities often found with explosives.

When a dimensional measurement is given for a part herein, the value is, unless explicitly stated or clear from the context, meant to describe an average for a necessary portion of the part, i.e., an average for the portion of the part that is needed for the stated purpose or function. Any accessory or excessive portion is not meant to be included in the calculation of the value.

The present invention is predicated on work aimed at detecting a variety of explosive analytes or chemicals and related materials in a given sample. In virtually all the prior art reports, when an explosive chemical interacts with a fluorophore, only quenching of the fluorescent emission occurs. See U.S. Patent Application 2009/0246881, and X. Sun, et al., *Chem. Soc Rev.*, 2015, 44, 8019-8061, the entire disclosure of which is incorporated herein by reference. To inventor's surprise, when the three-layer structure of the present invention was employed where an additional layer of thin polymer is placed underneath the fluorophores, first of all, enhancement of fluorescent emission, i.e., measurable increase in fluorescence intensity, was observed in many cases while signal quenching in some other cases. Still, negligible or no change was seen with the remaining sensor embodiments. Altogether, this makes it possible, for each explosive chemical tested, to generate a fluorescent signature or pattern that includes at least two of the following three optical responses: signal quenching, emission enhancement, and negligible change. What this transpired to was a new way to identify an explosive material using a binary or tertiary pattern without having to resort to further differentiating, among detected quenching, the degrees of changes. This opens up the number of explosives that can be identified while lowering requirements on the optical reader or spectrometer needed for the sensing apparatus as standard fluorescence pattern recognition techniques suffice. For example, pattern recognition could be achieved by Principal Component Analysis, Discriminant Analysis, Maximum Entropy Classification, Neural Networks, or other techniques well known to one of ordinary skills in the art.

A second surprise to the inventor was that alterations in the optical responses in the presence of an explosive were much stronger when using embodiments of the invention to test an analyte in its gas phase than previously when both the fluorophore and the analyte were dissolved in DMF solution. Changes ranging from about 100% quenching to greater than 100% enhancement of the fluorescent signal were observed and recorded using the present invention at room temperature and with explosive analytes in their gas phase. The stronger than expected responses make false positives less likely and detection easier, which means even visual inspection could work for some embodiments of invention, further reducing complexity and costs for manufacturing those embodiments.

Figure 8:
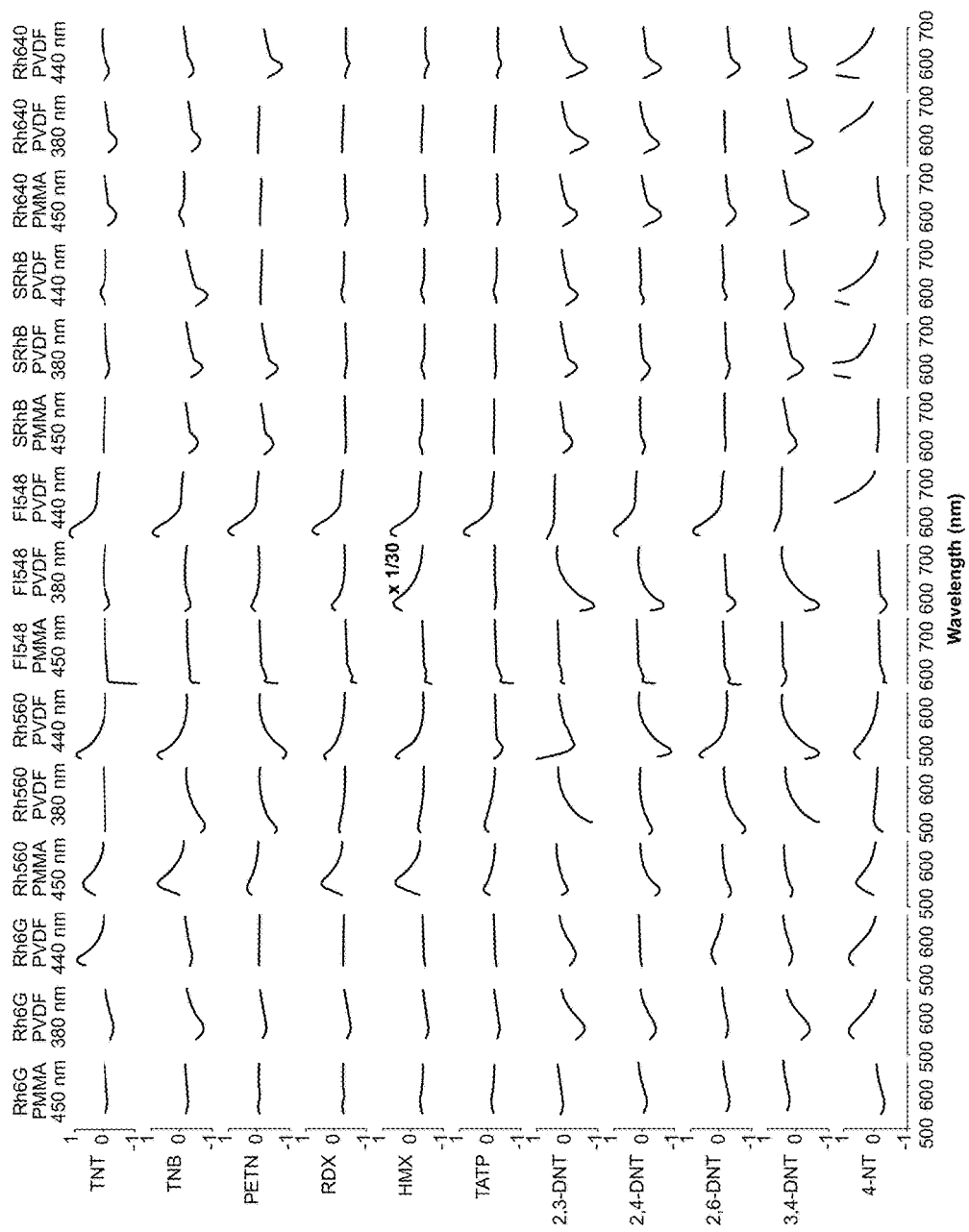
FIG. 8 shows normalized emission difference spectra for 15 different sensor composites exposed to 11 different analytes.

Yet a further unexpected finding was that for the same fluorophore/polymer combination, variance in the thickness of the polymeric layer could lead to completely different optical responses in the presence of the same analyte. This makes it possible that, with only a few polymer materials, unique fluorescent signatures or patterns can be generated for each and every target explosive of interest simply by varying the thickness of the polymeric layer as such adjustment can lead to differentiation among otherwise indistinguishable interactions with different analytes. In an example shown below, fluorescence difference spectrum was plotted for each of the 11 analytes as its fluorescent pattern, and each pattern was unique and distinguishable from each other, allowing identification of each of the 11 analytes used in this example (FIG. 8). With the availability to vary the intermediate layer thickness, only two different polymers—polymethylmethacrylate (PMMA) and polyvinylidene difluoride (PVDF)—and five different xanthene dyes (as fluorophores) were utilized in that example to accomplish the goal.

Figure 1:
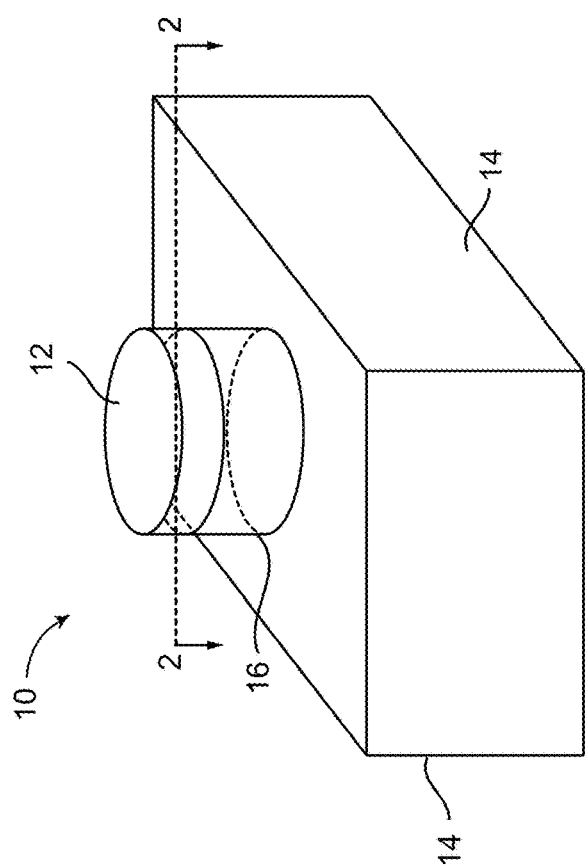
FIG. 1 illustrates a perspective view of an exemplary sensor embodiment according to the invention.

Referring now to FIGS. 1 and 2, in an exemplary embodiment to illustrate the principle of the invention, a sensor 10 is provided for detecting a chemical compound, e.g., an explosive or a related material. In between the conventional configuration of a top layer 12 that contains a fluorophore, and a substrate 14 for support, is added an intermediate layer 16 for amplifying an optical response from the fluorophore in the top layer 12. Both the intermediate layer 16 and the top layer 12 can be any size or shape in the horizontal dimension. In embodiments where the layers were printed onto the substrate 14, they are often circular in horizontal cross-section but can be other shapes. The top layer 12, sometimes referred to as a pixel or cell, is preferably a very thin layer of fluorophores, e.g., a monolayer. In an exemplary embodiment, the top layer 12 is about 2 mm in diameter, and between about 1 nm and about 10 nm in thickness.

While the intermediate layer 16 is depicted in FIG. 1 to have about the same horizontal cross section as the top layer 12, the intermediate layer 16 can be larger or smaller in cross section as long as it is in the light path for detection of the resultant fluorescence. The intermediate layer 16 is preferably transparent and made up by a material that has a refractive index that is less than that of the fluorophore in the top layer 12. In preferred embodiments, the intermediate layer 16 is made of one or more polymers. The intermediate layer 16 is preferably less than about 1000 nm, more preferably, less than about 800 nm, less than about 700 nm, and less than about 600 nm thick. Also, the intermediate layer 16 is preferably more than about 100 nm, and more preferably, more than about 250 nm, and even more preferably, more than about 350 nm thick.

The fluorophore that can be utilized in the top layer 12 for purpose of the present invention preferably has a high quantum yield that is no less than 0.20, preferably no less than 0.50, and more preferably no less than 0.80, or even no less than 0.90. As is known to one of ordinary skill in the art, a fluorophore with a high quantum yield, when dissolved in the appropriate solvent(s), natively give strong signals to start with. With further amplification of such signals by the intermediate layer 16, sensor sensitivity is markedly improved. In accordance, preferred fluorophore candidates for the invention include xanthene dyes, which are xanthene ($C_{13}H_{10}O$) derivatives and include fluoresceins, rhodamines, and eosins. Specific non-limiting examples of xanthene dyes useful for the present invention include: rhodamine 6G (Rh6G), rhodamine 560 (Rh560), rhodamine 640 (Rh640), sulforhodamine B (SRhB), and fluorescein 548 (Fl548).

In an embodiment, the refractive index for the selected fluorophore is between about 1.60 and about 1.80, and the polymer selected for the intermediate layer 16 has a refractive index between about 1.40 and 1.50 and are listed in FIG. 3. Specific non-limiting examples of polymers useful for the present invention include: PMMA, PVDF, poly(vinylidene difluoride-co-trifluoroethylene) ("co-polymer"), polypropylene, polyisobutylene and polystyrene (PS).

Referring back to FIGS. 1 and 2, the substrate 14 is preferably a rigid solid and can be of any dimension or configuration as long as it provides support to or houses the two layers 12 and 16. Specific non-limiting examples of solid materials useful as the substrate include: glass, flat silicon, porous silicon, metal (e.g., silver) coated porous silicon, metal, and a polymer different from the intermediate layer.

Figure 4:
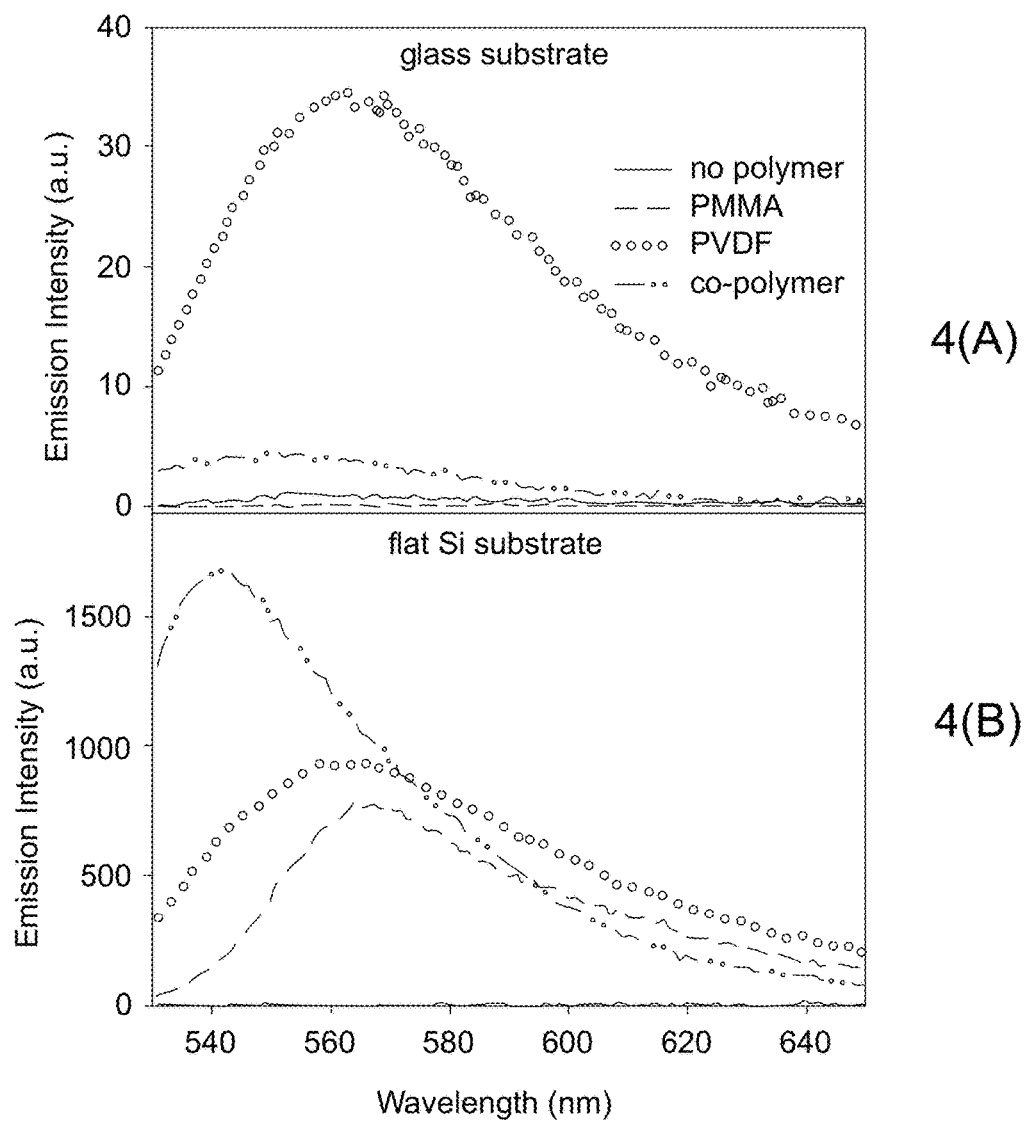
FIG. 4 shows emission spectra data of Rhodamine 6G coated on different polymers cast on a glass substrate (4A) and a flat silicon substrate (4B). All spectra are normalized to the spectrum with no polymer (solid line), PMMA (short dashes), PVDF (dotted line), and $[(CH_2CF_2)_{0.65}(CHFCF_2)_{0.35}]_x$—co-polymer (dot-dashed line).

FIG. 4 demonstrates the sensitivity of the sensor construction according to principles of the invention. The ordinate for each plot is the relative intensity of the Rh6G fluorescent emission detected in embodiments of the invention (with the polymer intermediate layer) compared to Rh6G deposited on a substrate with no polymer layer (i.e., defined as an emission maximum=1). As shown in FIG. 4A, when the substrate is a glass slide, boost of fluorescence could maximize at about 35 when PVDF is the polymer. Even more remarkably in FIG. 4B, when the substrate is flat silicon, fluorescence can be boosted to about 1600 with the co-polymer being the intermediate layer, about 1000 with PVDF, and about 700 with PMMA. This is one of the reasons why the sensors constructed according to principles of the invention are sensitive enough to detect explosives with vapor pressure in the parts per billion to parts per trillion range at room temperature.

Figure 5:
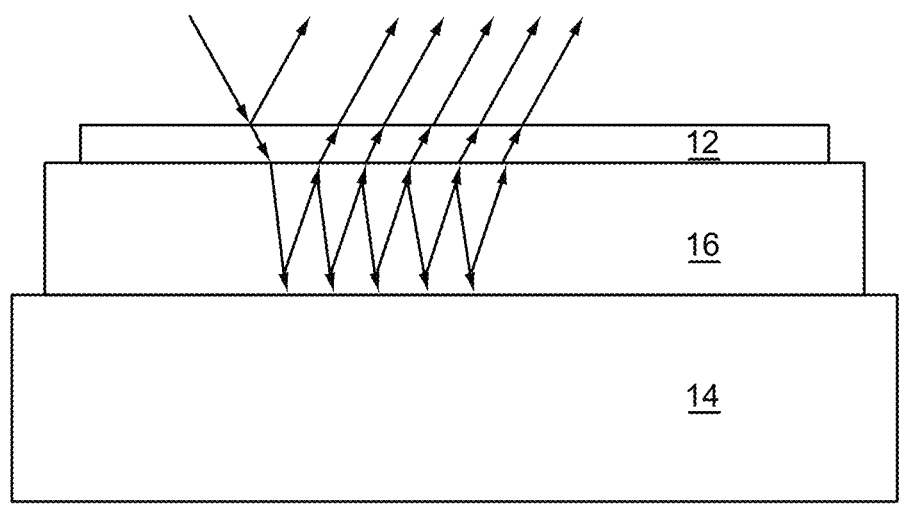
FIG. 5 schematically illustrates how an embodiment operates according to principles of the invention.

Referring now to FIG. 5, a simple model of internal reflection may account for the magnitude of the observed boost from adding a polymeric intermediate layer when the substrate is glass. In this model, some of the light is reflected at each interface, allowing light to bounce along the polymer layer. The internal reflection then provides more opportunities for the incident light to be absorbed, and subsequently emitted by the fluorophore.

Figure 6:
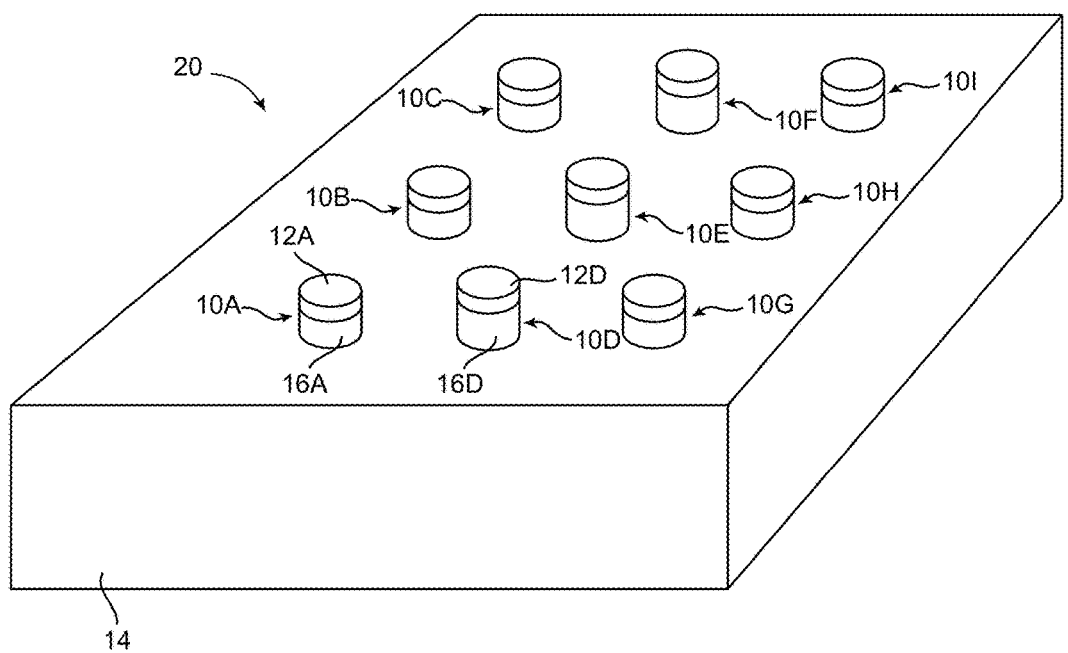
FIG. 6 illustrates a perspective view of an exemplary sensing system embodiment according to the invention.

Referring now to FIG. 6, an exemplary embodiment of a sensing system is shown to have multiple fluorescent sensors configured as described above. The sensing system 20 employs an array approach to counter the possibilities of false positives that detract from general usage of fluorescent sensors. While a given fluorophore may show similar signal alterations for several different analytes, the set of signals from several fluorophores is more likely to be unique. Furthermore, an unexpected discovery found that interactions between explosive analytes and the sensors of the present invention lead to not just the expected signal quenching, but emission enhancement as well as negligible change in emission. This reduces the number of sensors likely needed to generate a unique fluorescent pattern for each explosive analyte and related material.

Still referring to FIG. 6, the sensing system 20 includes multiple sensors 10A-10I, spread out on the substrate 14 in a 3×3 formation. Each of the sensors or pixels 10A-10I has the construction described in FIGS. 1 and 2. So, for example, sensor 10A has a top layer 12A with a fluorophore over an intermediate layer 16A preferably consisting essentially of a polymer, and so forth. Variables among the sensors at least include: makeup of the fluorophore, makeup of the polymer, and thickness of the polymer layer—any two sensors should differ in at least one of the variables. To illustrate, between sensors 10A and 10D: the top layers 12A and 12D may share the same dimensions and contain the same fluorophore at the same concentration; the intermediate layers 16A and 16D consist of the same polymer, e.g., PMMA, but the two polymeric layers may differ in thickness, enough to qualitatively change the optical response from some target analytes. And "qualitatively" changing, as used herein, means the optical response is altered from one of the following to another: signal quenching, negligible change and emission enhancement. In some embodiments, the difference in the thickness of the intermediate layer is more than 50 nm, 80 nm, or even 100 nm.

In making the sensor array, any conventional method of printing, coating or fixating the described layers to a solid substrate can be used. In one embodiment, a transparent polymer layer is first spin-cast onto the substrate with a predetermined thickness in the 100 to 1000 nm range. After that, a thin layer of fluorophore, about 1-10 nm thick, is spin-cast onto the polymer layer.

The sensing system further includes a light source (e.g., a xenon lamp or a UV light source) and an optional optical detector (e.g., a spectrometer or a CCD camera, and an optional optical filter). Optionally, the sensing system further includes, or is electronically connected to a processor where known patterns of target analytes are stored and compared to make an identification. The sensing system of the invention can be incorporated into a larger system, e.g., as a replaceable cartridge, or as a stand-alone instrument. The requirement on physical dimension is low enough to fashion a handheld embodiment for detection of explosives and related materials.

Figure 7:
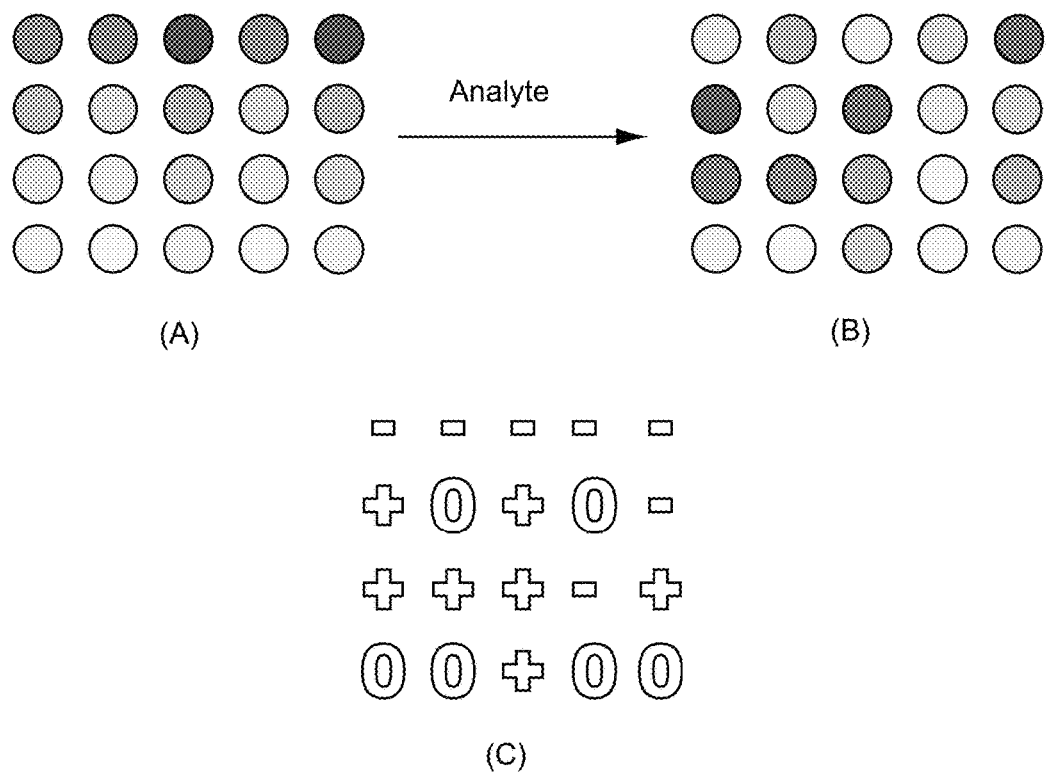
FIG. 7 schematically illustrates operation of an exemplary sensing system of the invention. The top illustrates alteration in fluorescent emission from a 4×5 array (from (A) to (B)) after exposure to an analyte. Panel (C) illustrates a tertiary readout from changes in fluorescent emission: enhancement ("+"), quenching ("−"), and negligible/no change ("0").

Referring now to FIG. 7, the sensing system of the present invention works as follows: first, emission intensities from all the pixels are measured and/or recorded; the sensing system is then exposed to an analyte, e.g., at room temperature at its natural vapor pressure; after a predetermined period, e.g., from a few seconds to about 10 minutes or longer, the emission intensities from all the pixels are re-measured and/or recorded; finally, changes in emission intensities from all the pixels are calculated to generate a readout (FIG. 7(C)). Based on a predetermined threshold, e.g., 5%, any change below the threshold is considered negligible and represented by a "0" in FIG. 7, while emission enhancement and signal quenching, both at or above the threshold, are represented by "+" and "−", respectively. This readout is then compared to known patterns of target analytes to see if one matches. In a preferred embodiment, the measurement, comparison, and identification steps are automatically performed by a processor to which the sensing system is in electronic and data communication with. However, because of the surprising strength in the optical responses from fluorophores detected using the invention before contact with analyte, and the often visible alterations in such optical responses after exposure to the analyte, it is possible to visually inspect the array and make comparison and identification with naked eye, offering an option for an ultra mobile and simple detection means for explosives and related materials. Non-limiting examples of explosives detectable by the sensing system of the invention include: TNT, TNB, PETN, RDX, HMX, and TATP.

EXAMPLES

The xanthene dyes used in this example, rhodamine 6G (Rh6G), rhodamine 560 (Rh560), rhodamine 640 (Rh640), sulforhodamine B (SRhB), and fluorescein 548 (Fl548), were obtained from Exciton, Inc. and used without further purification. Ethanol (95%), acetone, tetrahydrofuran (THF), and dimethylformamide (DMF) were obtained from Sigma Aldrich or Fisher Scientific and used without further purification. The dyes were dissolved in 95% ethanol at a concentration of $1.0 \times 10^{-4}$M for use in spin-coating. The polymers used, polymethylmethacrylate (MW 120,000, PMMA) and polyvinylidene difluoride (MW 534,000, PVDF), were obtained from Sigma Aldrich. PMMA was dissolved in toluene to form a 5% (w/v) solution. PVDF was dissolved in a solution of 9/1 (v/v) acetone/DMF at two concentrations, 2% (w/v) and 4% (w/v). Samples for spectroscopy were prepared by cleaning glass microscope slides in ethanol and then spin-coating the polymers onto the glass slide (acceleration of $1080 \, s^{-2}$ to 1200 rpm) under an atmosphere of dry nitrogen. This was followed by spin-coating the dye solutions onto the polymer layer. Exposure to the explosives analytes was done by placing the prepared slide in a vial containing a few mg of the analyte on the bottom of the vial. The cap on the vial was closed tightly and the slide exposed to the natural vapor pressure of analyte at room temperature for 10 minutes to 24 hours. Samples were then removed from the vial for spectroscopic analysis. A vial with no analyte was used as a control for each set of exposures. The analytes investigated were trinitrotoluene (TNT), trinitrobenzene (TNB), 1,3,5-trinitroperhydro-1,3,5-triazine (RDX), octahydro-1,3,5,7-tetranitro-1,3,5,7-tetrazocine (HMX), pentaerythritol tetranitrate (PETN), triacetonetriperoxide (TATP), 2,3-dinitrotoluene (2,3-DNT), 2,4-dinitrotoluene (2,4-DNT), 2,6-dinitrotoluene (2,6-DNT), 3,4-dinitrotoluene (3,4-DNT), and 4-nitrotoluene (4-NT).

Absorption measurements were made with a Perkin-Elmer Lambda 1050 spectrometer between 400 and 800 nm with a 2 nm slit width. An absorption spectrum of each sample was recorded prior to costing the fluorophore onto the polymer to be used for background correction. Reflection measurements were made with an Ocean Optics spectrometer between 400 and 1000 nm. Fluorescent measurements were made with a Jobin Yvon-Horiba Fluorolog spectrometer using a xenon lamp for excitation and 2 nm slit widths for both the excitation and emission monochomators and an integration time of 0.1 second. Fluorescent spectra were all corrected for the variations in the lamp intensity as a function of wavelength. Thickness measurements were made using the fringing patterns in the reflection and absorption spectra, when observed, or using a Filmetrics F40 thin film analyzer.

Computational results were done using Spartan 14. The spectra were computed using Time Dependent Density Functional Theory (TDDFT), the B3LYP functional, and the 6-311G* basis set. All structures converged with no imaginary frequencies.

Each of the polymer/fluorophore combinations was exposed to 11 different analytes composed of explosives or explosive-related materials. The sensing was done at room temperature with no heating of the analyte. Exposure times varied between 10 minutes and 24 hours but no changes were observed after 10 minutes. After the exposure, the absorption and emission spectra for each sample were re-measured. A few of the samples showed changes in the absorption spectra after exposure to analytes but the majority showed no changes (data omitted here). In contrast, most of the emission spectra exhibited intensity changes after exposure to an analyte. The normalized emission difference spectra are shown in FIG. 8.

The majority of the emission spectra show significant intensity alterations upon exposure to the analytes. The difference spectra displayed in FIG. 8 show both quenching and enhancement. And unexpectedly, the gas phase exposure gives much larger changes than the solution phase exposure. In DMF solution, the emission changes were typically a few per cent or less, except for TNT and TNB, which showed large changes because they reacted with the solvent. The results here show that the emission changes are typically on the order of a few tens of percent. This is despite the fact that in the solution the relative concentration of the analyte was orders of magnitude higher than the gas phase exposures presented here.

Figure 9:
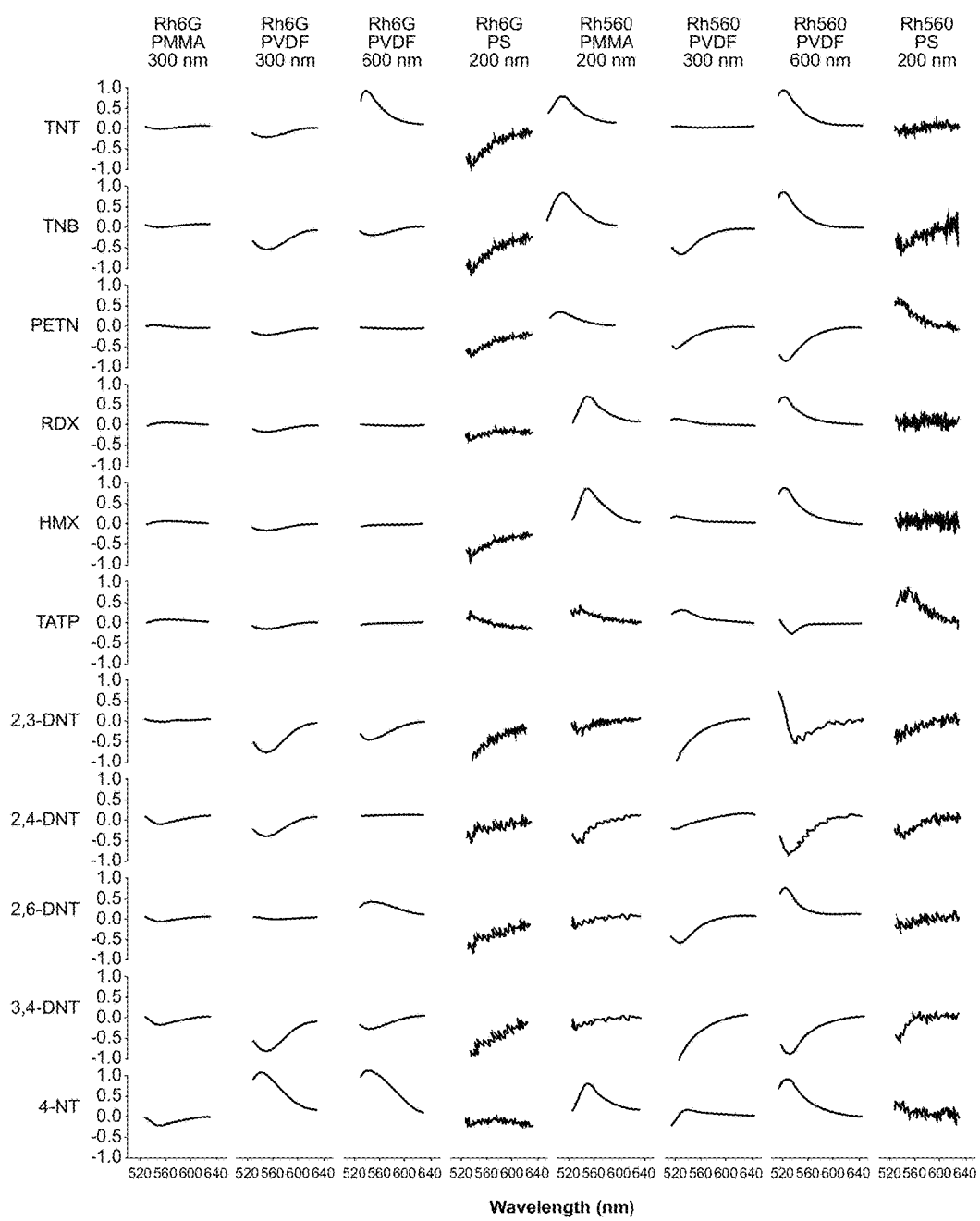
FIG. 9 shows normalized emission difference spectra for 8 different sensor composites exposed to 11 different analytes.

Results from another set of sensor array using two kinds of fluorophores (Rh6G and Rh560), three kinds of polymers (PMMA, PVDF, PS) at three difference thicknesses (200 nm, 300 nm and 600 nm) are presented in FIG. 9, where 11 analytes could be identified using their unique optical signatures generated in accordance with principles of the present invention.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A sensing system for identifying an analyte, the system comprising: a light source, an optical detecting system, and an array of sensors each supported on a substrate, each sensor comprising (a) a top layer comprising a fluorophore, and (b) an intermediate layer in between the top layer and the substrate for amplifying an optical response from the fluorophore,
    wherein the intermediate layer is between 100 nm and 1000 nm in thickness, consists essentially of one or more polymers and has a refractive index less than that of the fluorophore, and
    wherein at least two sensors in the array have respective intermediate layers that differ in thickness, such that when the light source is activated in the presence of an analyte in its gas phase, the optical detecting system would detect altered optical responses from the at least two sensors indicating signal quenching by at least 10% from one sensor and emission enhancement by at least 10% from the other sensor, thereby generating a fluorescent pattern for identifying the analyte by comparing the pattern to one or more target chemicals and wherein the substrate comprises a material selected from the group consisting of glass, flat silicon, porous silicon, and a polymer different from the intermediate layer.

2. The system of claim 1, wherein the intermediate layer is transparent.

3. The system of claim 1, wherein the one or more polymers are selected from the group consisting of polymethylmethacrylate (PMMA), polyvinylidene difluoride (PVDF), poly(vinylidene difluoride-co-trifluoroethylene), polypropylene, polyisobutylene and polystyrene (PS).

4. The system of claim 1, wherein the average refractive index of the fluorophores in each pixel is no less than about 1.60.

5. The system of claim 1, wherein the fluorophore comprises a xanthene dye.

6. The system of claim 1, wherein the fluorophore has high quantum yield that is no less than 0.20.

7. The system of claim 1, wherein the intermediate layer is more than about 250 nm thick.

8. The system of claim 1, wherein the intermediate layer is less than about 800 nm thick.

9. The system of claim 1, wherein the optical detecting system comprises a spectrometer or a CCD camera.

10. The system of claim 1, wherein the optical detecting system comprises an optical filter.

11. The system of claim 1, further comprising a processor.

12. The system of claim 11, wherein the processor, based on expected spectral response from a target explosive or related material, determines if the target is in the analyte.

13. The system of claim 11, wherein the target explosive or related material is selected from the group consisting of TNT, TNB, PETN, RDX, HMX, TATP, 2,3-DNT, 2,4-DNT, 2,6-DNT, 3,4-DNT and 4-NT.

14. The system of claim 11, wherein the processor, categorizes optical responses from all sensors into one of three values based on a preselected threshold in detected changes in fluorescence intensity: enhancement, quenching, and no change.

15. The system of claim 14, wherein the threshold is about 20%.

16. A method for detecting an explosive or related material, the method comprising:
    (a). providing a fluorophore-based sensing system that comprises an array of sensors each supported on a non-metal substrate, each sensor comprising (i) a top layer comprising a fluorophore, and (ii) an intermediate layer consisting essentially of one or more polymers, more than 100 nm thick, and disposed in between the top layer and the substrate in each sensor, wherein the array of sensors are pre-selected with different fluorophore/polymer combinations among them so that optical responses from some or all sensors will be altered and result in signal quenching by at least 10% in at least one sensor and emission enhancement by at least 10% in at least another sensor in the presence of a target explosive or related material in a gas phase;
    (b). exposing the sensing system to an analyte-containing sample;
    (c). detecting altered optical responses from each sensor;
    (d). comparing detected optical responses to a pattern known to come from a target explosive or related material; and
    (e). determining whether they are similar enough to identify the analyte as the target explosive or related material.

17. The method of claim 16, wherein the explosive is selected from the group consisting of nitroaromatics, nitroamines, organic nitramides, and organic nitrates.

18. The method of claim 16, wherein the explosive or related material is selected from the group consisting of TNT, TNB, PETN, RDX, HMX, TATP, 2,3-DNT, 2,4-DNT, 2,6-DNT, 3,4-DNT and 4-NT.

19. The method of claim 16, wherein the one or more polymers are selected from the group consisting of polymethylmethacrylate (PMMA), polyvinylidene difluoride (PVDF), poly(vinylidene difluoride-co-trifluoroethylene), polypropylene, polyisobutylene and polystyrene (PS).

20. The method of claim 16, wherein the different fluorophore/polymer combinations among sensors result from at least one variables selected from the group consisting of makeup of the fluorophore, makeup of the polymer, and thickness of the intermediate polymer layer.

21. A sensing system for detecting an explosive in a gas phase, the system comprising an array of sensors each supported on a non-metal substrate, each sensor comprising (a) a top layer comprising a fluorophore, and (b) an intermediate layer in between the top layer and the substrate for amplifying an optical response from the fluorophore, wherein the intermediate layer consists essentially of one or more polymers selected from the group consisting of polymethylmethacrylate (PMMA), polyvinylidene difluoride (PVDF), poly(vinylidene difluoride-co-trifluoroethylene), polypropylene, polyisobutylene and polystyrene (PS), is more than 100 nm thick and has a refractive index less than that of the fluorophore, and wherein each sensor in the array is different from each of the remaining sensors in at least one of three aspects: thickness of its intermediate layer, makeup of the polymers in its intermediate layer or the makeup of the fluorophore.

22. The system of claim 21, wherein the fluorophore comprises a xanthene dye.

23. The system of claim 1, wherein the intermediate layer is more than about 350 nm thick.

24. The system of claim 1, wherein at least two sensors in the array have respective intermediate layers that differ in the makeup of their polymers.

\* \* \* \* \*